May 10, 1955 M. ROBICHON Plant Pat. 1,392
ROSE PLANT
Filed Sept. 10, 1954
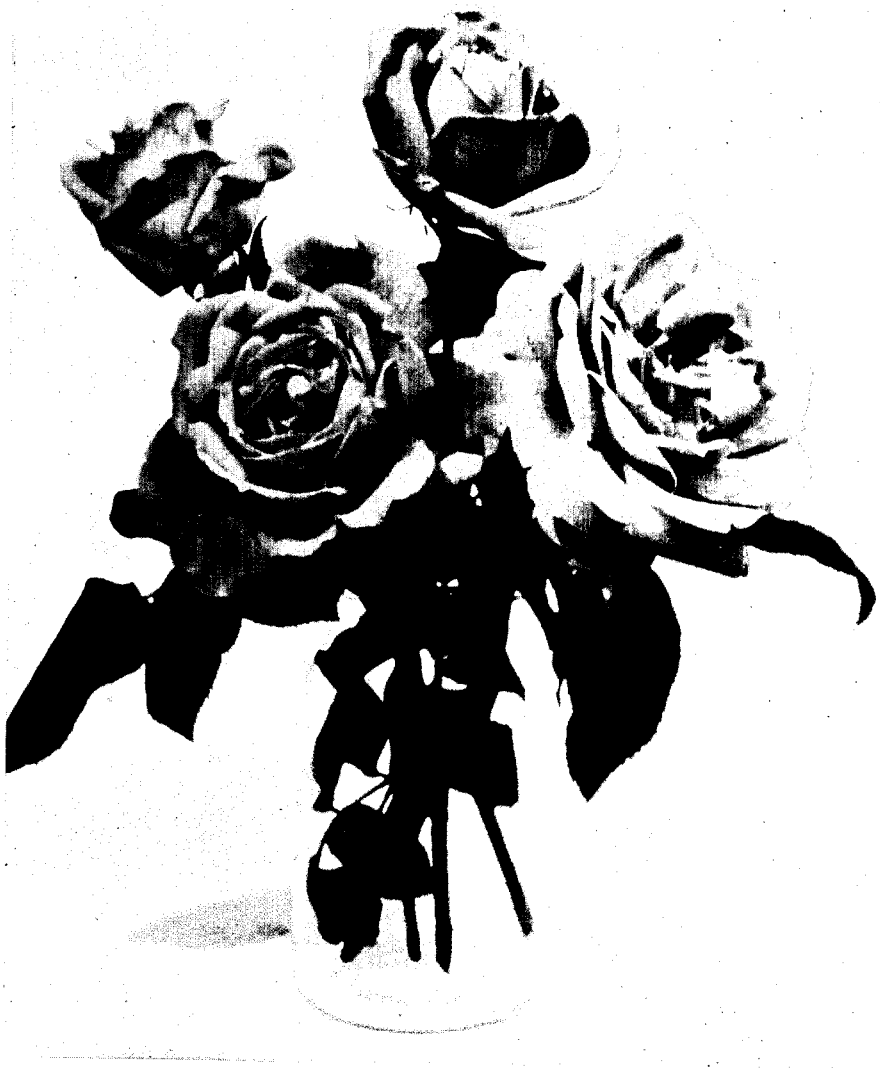
Inventor
Marcel Robichon
By: Robb & Robb
Attorneys United States Patent Office Plant Pat. 1,392
Patented May 10, 1955

1,392

ROSE PLANT

Marcel Robichon, Pithiviers, France, assignor to Ilgenfritz Nurseries, Inc., Monroe, Mich., a corporation of Michigan Application September 10, 1954, Serial No. 455,371

1 Claim. (Cl. 47—61)

The present invention relates to a new and distinct variety of rose plant of the hybrid tea class, which was originated by me by crossing an unnamed and unpatented seedling derived from a cross of "Hadley" (unpatented) × "Ami Quinard" (unpatented), with the variety "Crimson Glory" (Plant Patent No. 105).

As the result of this breeding, I have produced a new variety of rose plant which is particularly characterized as to novelty by its vigorous, strong and floriferous habits of growth, its relatively stiff flower stems which make the flowers stand better both on the bush and as cut flowers, its comparatively few thorns, and the relatively large size, strong tea fragrance and distinctive color of its flowers, said flowers having a true Blood Red general color tonality, with shadings of Garnet. From this unique combination of characteristics, it is fully evident that my new variety is definitely distinguished from its parents, as well as from all other varieties of its class heretofore known to me, and in particular, it is more floriferous than most other well-known varieties such as "Charles Mallerin" (Plant Patent No. 933), "Crimson Glory" (Plant Patent No. 105), "Happiness" (Plant Patent No. 911) and "New Yorker" (Plant Patent No. 823).

Asexual reproduction of my new variety by budding, as performed in France, as well as at Monroe, Michigan, U. S. A., shows that the foregoing characteristics and distinctions come true to form and are established and transmitted through succeeding propagations.

The accompanying drawing shows typical specimens of the flowers and foliage of my new variety in different stages of development, and as depicted in color as nearly true as it is reasonably possible to make the same in a color illustration of this character.

The following is a detailed description of my new variety, with color terminology in accordance with Horticultural Color Charts I and II issued by The British Colour Council in collaboration with The Royal Horticultural Society, except where general color terms of ordinary dictionary significance are obvious:

Type: Hardy; bush; greenhouse and outdoor; seedling; for cut flowers and for garden decoration.
Class: Hybrid tea.
Breeding: Seedling.
*Seed parent.*—An unnamed seedling of "Hadley × "Ami Quinard."
*Pollen parent.*—"Crimson Glory."
Propagation: Holds its distinguishing characteristics through succeeding propagations by budding.

FLOWER

Locality where grown and observed: Pithiviers, Loiret, France, and Monroe, Michigan, U. S. A.
Continuity: Continuous.
Fragrance: Strong. Nature—tea.
Flowers borne: Singly; on long, relatively stiff stems.
Quantity of bloom: Abundant, both outdoors and in greenhouse.

Bud:
*Peduncle.*—Long; heavy; erect; stiff; with a few red thorns. Color—Green-Bronze.
*Before calyx breaks.* — Size — medium. Form—pointed; with a conspicuous neck; with foliaceous appendages on the surface of the bud; with bristle-like foliaceous parts extending beyond the tip of the bud equal to ½ or more of its length. Color—Fern Green, Plate o862/1.
*As calyx breaks.*—Color—Chrysanthemum Crimson, Plate 824/1.
*As first petal opens.*—Size—large. Form—pointed. Color: outside—Spiraea Red, Plate o25; inside—Cardinal Red, Plate 822/2.
*Opening.*—Opens up well.
Bloom: Size (when fully open)—very large; from 4 inches to 5 inches.
*Petalage.*—Double; from 45 to 60 petals; arranged irregularly.
*Form.*—Very full and high-centered, becoming cupped; petals being at first tightly cupped and rolled outward, but becoming later at maturity cupped and rolled outward.
Petals: Thick; leathery; with inside velvety and outside satiny.
*Shape.*—Outside—round, with 3 notches. Intermediate—round, with 3 notches. Inside—round, with 3 notches.

This description of a newly opened flower was made from a rose grown outdoors in the month of June, at Monroe, Michigan, U. S. A.:

Color:
*Outside petal.*—Outside surface—Spiraea Red, Plate o25. Inside surface—Cardinal Red, Plate 822/2.
*Intermediate petal.*—Outside surface—Spiraea Red, Plate o25. Inside surface—Cardinal Red, Plate 822/2.
*Inner petal.*—Outside surface—Spiraea Red, Plate o25. Inside surface—Cardinal Red, Plate 822/2.

This description was made from a rose that was open for 3 days outdoors in the month of June, at Monroe, Michigan, U. S. A.:

Color:
*Outside petal.*—Outside surface—Chrysanthemum Crimson, Plate 824/3. Inside surface—Chrysanthemum Crimson, Plate 824/1.
*Inside petal.*—Outside surface—Magenta Rose, Plate o27. Inside surface—Tyrian Purple, Plate 727.
General color effect:
*Newly opened flower.*—Chrysanthemum Crimson, Plate 824/1.
*3-days open.*—Chrysanthemum Crimson, Plate 824/2.
Behavior: Drop off cleanly; slight tendency to darken with dry and hot weather.
Flower longevity: On bush in garden—5 days in June. Cut flowers grown outdoors and kept at living-room temperatures—5 days in June.

REPRODUCTIVE ORGANS

Stamens: Medium number; arranged irregularly about pistils. Color—Naples Yellow, Plate 403/1.
Filaments: Medium length; few with anthers. Color—Solferino Purple, Plate 26/2.
Anthers: Medium size; all open at once. Color—Yellow Ochre, Plate o7.
Pollen: Moderate abundance. Color—Cadmium Orange, Plate 8/2.
Pistils: Few.

Styles: Uneven; medium length; very heavy; bunched.
Stigma: Color—White.
Ovaries: All enclosed in calyx.
Hips: Globular; smooth; walls fleshy. Color—Reddish.
Sepals: Falling soon; long; recurved. Color—Reddish Green.
Seeds: Few; large.

PLANT

Foliage:

*Leaves.*—Compound of 5 leaflets; normal abundance; large; glossy.

*Leaflets.*—Lanceolate, with apex obtuse; round base; margin doubly dentate.

*Color.*—Mature: upper surface—green; under surface—Grey. Young: upper surface—Red; under surface—Dark Red.

*Rachis (the supporting stem of the compound leaf.)* — Light. Upper side — smooth. Under side—sparsely thorny.

*Stipules.*—Short; medium width; with medium length points turning out at an angle.

*Disease resistance.*—Above average resistance to mildew and blackspot as compared with other varieties grown under comparable cultural conditions at Monroe, Michigan, U. S. A.

Growth:

*Habit.*—Upright; much-branched.

*Growth.*—Free; vigorous.

*Canes.*—Heavy.

*Main stems.*—Color—Red. Thorns—few; straight; with short base. Prickles—few. Color—Red. Hairs—few. Color—Red.

*Branches.*—Color—Red. Thorns—few; straight; with short base. Prickles—few. Color—Reddish. Hairs—few. Color—Reddish.

*New shoots.*—Color—Red. Thorns—few; short; with short base. Prickles—few. Color—Reddish. Hairs—few. Color—Reddish.

I claim:

A new and distinct variety of rose plant of the hybrid tea class, substantially as herein shown and described, characterized particularly as to novelty by its vigorous, strong and fluoriferous habits of growth, its relatively stiff flower stems, its comparatively few thorns, and the relatively large size, strong tea fragrance and distinctive color of its flowers which have a true Blood Red general color tonality, with shadings of Garnet.

No references cited.